United States Patent [19]

Ries et al.

[11] 4,305,297

[45] Dec. 15, 1981

[54] ULTRASONIC TESTING OF WELD SEAMS OF PIPES FOR DETECTING TRANSVERSELY EXTENDING DEFECTS

[75] Inventors: Karl Ries, Mülheim; Kurt Hannoschöck, Sonsbeck; Heinz Schneider, Düsseldorf, all of Fed. Rep. of Germany

[73] Assignee: Mannesmann Aktiengesellschaft, Düsseldorf, Fed. Rep. of Germany

[21] Appl. No.: 65,578

[22] Filed: Aug. 10, 1979

[30] Foreign Application Priority Data

Aug. 11, 1978 [DE] Fed. Rep. of Germany ....... 2835680

[51] Int. Cl.³ ............................................. G01N 29/04
[52] U.S. Cl. ......................................... 73/628; 73/622
[58] Field of Search ................. 73/623, 625, 628, 622, 73/629, 638

[56] References Cited

U.S. PATENT DOCUMENTS

| | | | |
|---|---|---|---|
| 3,575,044 | 4/1971 | Gibbs | 73/625 X |
| 3,850,027 | 11/1974 | Nakanishi et al. | 73/625 X |
| 3,868,847 | 3/1975 | Gunkel | 73/622 |
| 3,888,114 | 6/1975 | Adams, Jr. et al. | 73/628 |
| 4,010,636 | 3/1977 | Clark et al. | 73/638 |
| 4,137,779 | 2/1979 | Wüstenberg et al. | 73/628 X |

*Primary Examiner*—Daniel M. Yasich
*Attorney, Agent, or Firm*—Smyth, Pavitt, Siegemund & Martella

[57] ABSTRACT

Ultrasonic test equipment for testing the welding seam a thick wall includes transducers arranged in tandem and along the welding seam, whereby a tandem pair inspects in any instance two surface-near zones (inner and outer surface) as well as an interior zone. One of the transducers of the pair participates in a function test. Two pairs cover the same zones, but from opposite sides.

2 Claims, 1 Drawing Figure

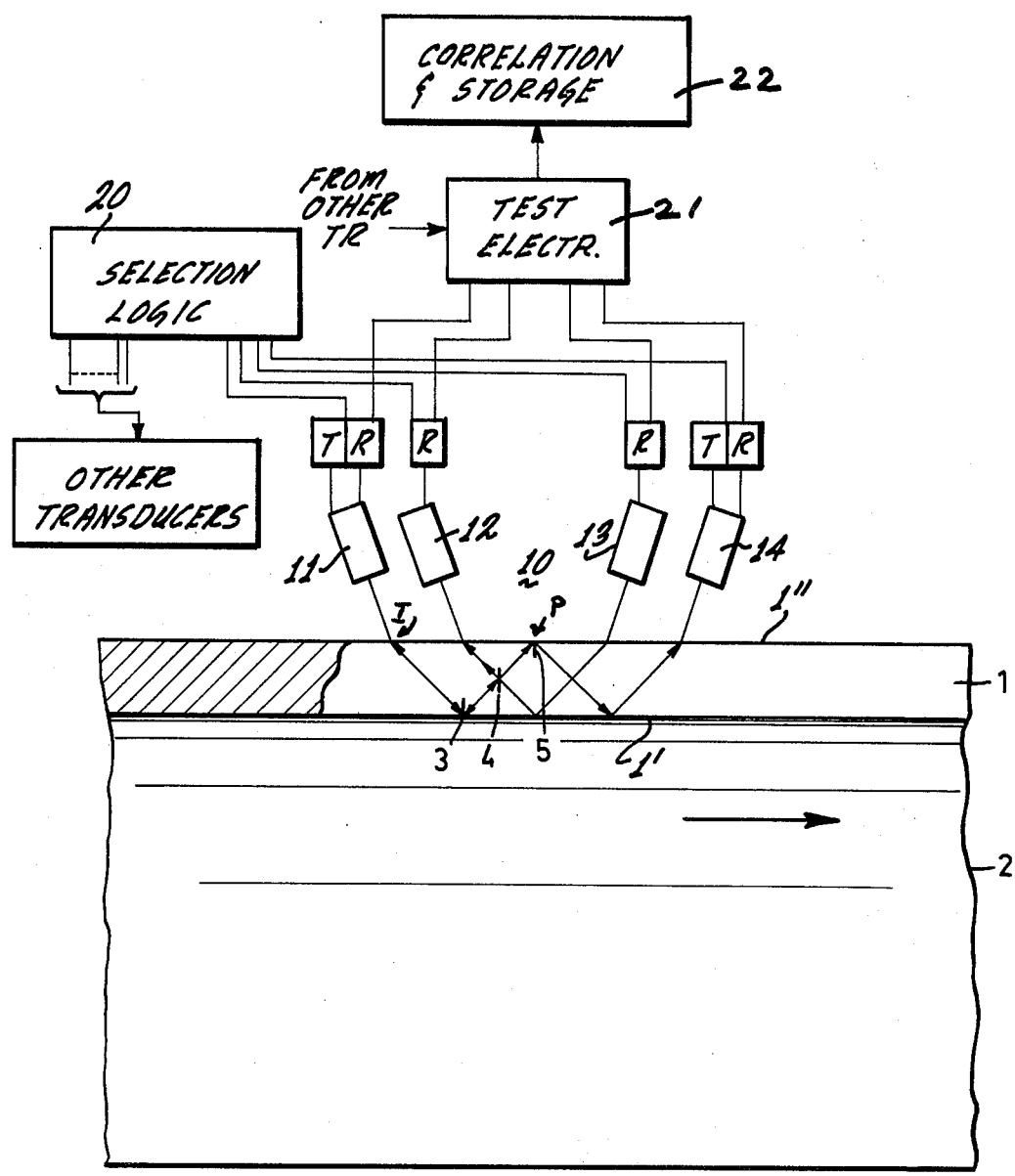

ULTRASONIC TESTING OF WELD SEAMS OF PIPES FOR DETECTING TRANSVERSELY EXTENDING DEFECTS

BACKGROUND OF THE INVENTION

The present invention relates to the testing and inspection of welding seams by means of ultrasonics, and more particularly the invention relates ultrasonic testing of the seam of submerged arc-welded pipes of large and thick pipes (e.g., wall thickness in excess of an inch).

U.S. Pat. No. 4,131,026 granted to one of us with other inventors refers to test procedures of the type referred to above. The method and system as described therein passes the pipe with seam longitudinally through a plurality of test stations being spaced apart (longitudinally as well as laterally) in a well-defined manner, so that different portions of the seam are tested in each instant, but all portions pass adjacent to, or even under, all of the stations. All tests are cyclically repeated in steps, and the individual test results are correlated with each other on the basis of the pipe's advance; these test results are essentially particular transit times of echos (or absence thereof within specifiable periods), amplitude limits, etc. This way, one obtains quite accurately a localized representation of transverse and/or longitudinal defects and flaws as well as of edge zone defects.

The patent referred to above discloses particularly ultrasonic transducers to be disposed directly above the welding seam (or below) and directing test beams, having (a) a component towards the seam, (b) a component in the longitudinal direction of seam and pipe advance, and (c) no component in transverse direction.

Previously and elsewhere, one tests a seam for locating transversely extending flaws by means of test heads, which are also laterally displaced from the seam, but the test beams provide also the components (a) and (b). (See, e.g., U.S. Pat. No. 3,868,847.) Depending on the type of arrangement, one calls those methods V or X test methods. The X and V methods are characterized by the fact that the transmitting transducer cannot serve also as a receiving transducer as far as the detection of a transversely extending crack is concerned, because the cracks (except in very rare instances) will not reflect any significant amount of ultrasonic energy towards the transmitter. For a complete inspection, one needs therefore a comparatively large number of such transducers, particularly when the seam and pipe wall is rather thick.

It should be noted that modern ultrasonic test equipment uses a coupler fluid (e.g., water) between the test heads and the test object. Thus, the test heads do not directly engage the object. It is primarily for this reason that multiple heads are needed in X or V arrangement to make sure that the zones and regions to be inspected are adequately covered.

Whenever one needs, for any reason, separate receivers and transmitters, installation and, particularly, adaptation to different sizes of the test object is made complicated in that the beam path is dependant in each instance upon two heads and their position. Generally speaking, this makes it impossible to provide for a controlled change of but one test parameter while maintaining the others constant. For example, the transmitting transducer head has a particular transmitter lobe along its axis and the receiving transducer has also a particular receiver lobe along its axis. Changing the position and orientation of one requires always a corresponding change of the other because the test requires a particular mutual orientation of these heads to each other, through the test object and the coupler fluid (twice). The first-mentioned patent avoids these problems to some extent, but it was found that thick pipes and correspondingly thick seams are not adequately tested by just two transducers. This is not immediately apparent because seemingly any defect intercepting a test beam propagating into the interior of a seam should produce, e.g., a noticeable and detectable response. Nevertheless, it has been discovered that, for example, flaw detection through pulse echos is more or less limited to surface-near cracks; the X or V methods are not sufficiently sensitive anyway.

DESCRIPTION OF THE INVENTION

It is an object of the present invention to improve ultrasonic testing of the seam of thick-walled pipes so that defects in the interior of the seam will also be located.

It is another object of the present invention to improve ultrasonic test methods and equipment, using a plurality of test heads for inspecting a welding seam for the purpose of locating longitudinal and transverse defects as well as edge defects, the improvement being related particularly to the detection of transversely extending defects.

In accordance with the preferred embodiment of the present invention, it is suggested to provide a pair of transducers in a tandem arrangement, one behind the other, along the welding seam with parallel but obliquely oriented axes. One of the transducers is operated as transmitter for ultrasonic test pulses; and in one phase, it is switched over immediately, to receive echos particularly from surface-near defects, if there are any, while in the same or in another phase the second transducer responds to reflections of the test beam by any transverse, interior defect. This tandem system may be duplicated symmetrically so that each seam portion is inspected, so to speak, from opposite sides; moreover, one transducer per pair can be used together for an equipment function test.

The preferred embodiment of the invention, the objects and features of the invention, and further objects, features and advantages thereof will be better understood from the following description taken in connection with the accompanying drawings.

DESCRIPTION OF THE DRAWING

The FIGURE illustrates a pipe to be tested by means of schematically illustrated test equipment.

Proceeding now to the detailed description of the drawing, FIG. 1 shows the portion of a pipe 2, the section being taken longitudinally through a welding seam 1. The section lines have been omitted in parts to better illustrate relevant test paths. This seam is to be tested and inspected for defects, and the particular equipment illustrated inspects the seam for defects which extend transversely to the plane of the drawing or have at least a significant component of extension in that direction.

The particular test equipment 10 includes two pairs (11,12 and 13,14) of transducers, whereby the transducers of a pair, 11 and 12 or 13 and 14, are arranged in tandem. That is to say, they are arranged to have parallel axes for transmission and/or receiving, and these axes are arranged at oblique angles to the surface of pipe 2. Moreover they are arranged one behind the other, above the welding seam and in the longitudinal direction of extension of that seam along which direction the pipe moves during the test (arrow).

On the other hand, the two pairs of test heads have their axes pairs inclined towards each other for the reason of coverage. All heads are acoustically coupled to the pipe by means of water; a certain quantity is maintained between heads and pipe so that the angle of refraction of any test beam is determined by the acoustic properties adjacent to a water-steel interface. It should be noted that actually the test equipment may be placed under the pipe, the seam being in the 6 o'clock position. The mechanical structure for such a test equipment is shown, for example, in U.S. Pat. No. 4,131,027 granted to one of us and others.

The test heads are under control of a test circuit which operates these heads within a larger system. The test circuit for this system includes a selection circuit 20 which enables the various heads, e.g., in controlled sequence, and determines whether and when they should operate as transmitters or as receivers. Accordingly, all heads are selectively, operatively connectable to a receiver circuit R (preamplifier), and at least some transducer heads (e.g., 11 and 14) are also selectably connectible to transmitter circuits T.

The receiver circuitry for all heads are all connected to a common input channel and amplifier, being part of a test electronics 21, and which receives any signal picked up by a head when enabled and operated as a receiver. Of course, channel or circuit 21 includes noise suppression and, preferably, gates which are selectively enabled to restrict the response for particular tests to particular periods of time (looking window); a signal received within such a period, or absence of a signal within such a period, is of direct significance for the inspection and/or function test of the equipment itself. Channel 21 includes signal detection, amplitude discrimination, and transit time measuring circuits; and it is connected to circuits 22 for storing these values and correlating them.

Selection logic 20 provides for a sequence of cycles or steps, whereby, in each cycle, one particular test is performed, the result evaluated, which is followed by another cycle, etc., for a test sequence which involves all of the transducers, in several instances repeatedly; subsequently, the sequence of cycles is repeated periodically, ultimately to inspect the entire welding seam. Correlation logic 22 will correlate different tests performed at different times on the same seam portion to verify and localize any defect. Circuitry usable for this purpose is disclosed, e.g., in U.S. Pat. No. 4,173,898 (Ser. No. 816,149, filed July 15, 1977).

As far as the illustrated portion of this test equipment is concerned, they may be operated in the following sequence of individual tests and test cycles, being included in a larger sequence, as outlined above.

Test n, head 11 alone is enabled and operated at first as transmitter to launch a pulse; it is switched over shortly thereafter (after transient decay) to the receiver mode to receive (always) a scatter echo from the upper surface. These types of echos are usually used as a timing reference.

Presently, it is assumed that the defects, 3 and 5, are in the range of that beam. Clearly, they produce pronounced echos well exceeding in amplitude any rear-wall echo and any second-front wall echo, and are thus identifiable as flaw echos. If the defects are not present, only insignificant echos will be produced by the inner surface 1' and the outer surface 1". None of the other heads participates in that particular test. However, the function test (n+2, infra) could be produced also as the transit times involved are far apart. For reasons of equipment sharing, it is, nevertheless, impractical to use more than one transducer as an input for the receiver and evaluating circuits 21 and 22 during one test cycle.

Test n+1, head 11 is again operated as ultrasonic pulse transmitter, but head 12 is operated as receiver. Head 12 will not receive any reflection (except diffracted noise), unless the beam is intercepted by a defect. Reference numeral 4 denotes such a defect, being located in the interior of the welding seam. This defect will reflect a portion of the incident beam towards head 12.

It can thus be seen that head 12 should be located at the chosen orientation, about halfway between the point I of which the axis of transducer 11 intersects the outer surface 1' the seam, and a point P of reflection of a beam along that axis at this outer-seam surface. However, this is not mandatory. Rather, the detection ranges of the transducers as to surface-near defects, on one hand, and for detecting interior defects, on the other hand, may normally largely overlap. Thus, the pipe's wall thickness may vary accordingly, and complete inspection is still ensured. If the pipe's wall and the seam are much thicker still, a third, tandem-operated transducer may be added (or may already have been provided for this purpose).

Test n+2, head 11 transmits and head 14 receives. This test cycle is not a test for locating defects, but is run as an on-line diagnostic test for test equipment. Head 14 will not receive any echo, but the directly transmitted test pulse.

Test N+3, head 14 operates as transmitter, but is switched over to the receiving mode. In this particular case, defect 5 should also produce a pronounced echo, which can be used for verification and localization of the defect.

Test n+4, head 14 transmits and head 13 receives. This test cycle represents the analogous situation for detecting interor defects. In the illustrated situation, no defect will be detected. However, after the tube has progressed, defect 4 should be in the range of the test beam from transmitter 14, and defect 4 should be located again.

Another function test could involve head 14 as transmitter and head 11 as receiver. Also, one of the heads 12 and 13 can be operated as a transmitter, the other one as a receiver for the purpose of diagnostics though for a regular test program proper these two transducers do operate as receivers only in the respective tandem arrangement.

The invention is not limited to the embodiments described above, but all changes and modifications thereof not constituting departures from the spirit and scope of the invention are intended to be included.

We claim:

1. A method of testing a welding seam of thick-walled pipes with regard to transversely extending defects and as part of a test program which includes other tests such as tests for locating longitudinal defects, a pipe moving in axial direction during and pursuant to a test program, comprising the steps of arranging and providing at least two transducers, one behind the other along the seam as seen in the direction of movement, and with similar, oblique angles of incidence, and a third transducer being arranged to one of the transducers of said two transducers along said seam with a similar but oppositely oriented angle of reflection;

(i) operating one of the two transducers as transmitter in a first test step, the other one of the two transducers as a receiver, for locating in the interior of the seam transverse defects which intercept the transmitted test beam after having been reflected on an inside surface of the seam, and deflect a portion towards said other transducer, if such an interior defect is present;

(ii) operating said one of the two transducers also as a receiver in a second test step for locating surface-near, transversely extending defects by detecting echos from such defects; and (iii) operating one of the two transducers as a transmitter and the third one as a receiver in a third test step, these test steps being carried out sequentially.

2. A method as in claim 1, and including a fourth transducer arranged in tandem with the third transducer and along said seam, and including the steps of operating the third and fourth transducers analogously to operating steps (i) and (ii).

* * * * *